United States Patent [19]
Schultz et al.

[11] Patent Number: 6,033,911
[45] Date of Patent: Mar. 7, 2000

[54] AUTOMATED ASSAYING DEVICE

[75] Inventors: Harold R. Schultz; Gregory Gulla, both of Reno; James E. Johnson, Incline Village, all of Nev.

[73] Assignee: Hamilton Company, Reno, Nev.

[21] Appl. No.: 09/032,741

[22] Filed: Feb. 27, 1998

[51] Int. Cl.[7] .................................... G01N 1/14
[52] U.S. Cl. ................ 436/49; 436/47; 436/54; 436/180; 422/63; 422/65; 422/100; 422/103; 422/81; 73/863.32; 73/863.24; 73/863.25
[58] Field of Search .................. 436/43, 49, 54, 436/174, 180; 422/63, 65, 81, 100, 103, 104; 73/863.32, 863.24, 863.25; 141/1, 130, 180, 181, 237, 238

[56] References Cited

U.S. PATENT DOCUMENTS

| | | | |
|---|---|---|---|
| 3,568,735 | 3/1971 | Lancaster | 141/238 |
| 3,776,700 | 12/1973 | Gallant | 422/100 |
| 4,106,911 | 8/1978 | Marcelli | 422/100 |
| 4,276,048 | 6/1981 | Leaback | 422/65 |
| 4,621,665 | 11/1986 | Webb | 141/1 |
| 4,844,298 | 7/1989 | Ohoka et al. | 222/58 |
| 4,952,518 | 8/1990 | Johnson et al. . | |
| 5,055,263 | 10/1991 | Meltzer . | |
| 5,108,703 | 4/1992 | Pfost et al. | 422/65 |
| 5,114,681 | 5/1992 | Bertoncini et al. . | |
| 5,226,462 | 7/1993 | Carl . | |
| 5,262,128 | 11/1993 | Leighton et al. . | |
| 5,306,510 | 4/1994 | Meltzer . | |
| 5,334,352 | 8/1994 | Johnson . | |
| 5,395,594 | 3/1995 | Nokihara et al. . | |
| 5,497,670 | 3/1996 | Carl . | |
| 5,525,302 | 6/1996 | Astle . | |
| 5,531,959 | 7/1996 | Johnson et al. . | |
| 5,660,792 | 8/1997 | Koike . | |

OTHER PUBLICATIONS

Packard, "MultiPROBE Robotic Liquid Handling Systems", Dec., 1996, entire brochure (12 pages).

Stanchfield, J., et al. "Precision 96–Channel Dispenser for Microchemical Techniques", Product Application Files, vol. 20, No. 2 pp. 292–296, 1996.

*Primary Examiner*—Long V. Le
*Attorney, Agent, or Firm*—Bernhard Kreten

[57] ABSTRACT

An automated assaying system is disclosed having a multiplicity of lumens oriented and controllable in clusters. The lumens are portrayed in a matrix, wherein each row of the matrix consists of one such cluster that is individually controllable for aspiration and dispensation purposes. Also provided is a unique wash system capable of flushing the entirety of the system. A method is also depicted for accomplishing this unique assaying.

23 Claims, 10 Drawing Sheets

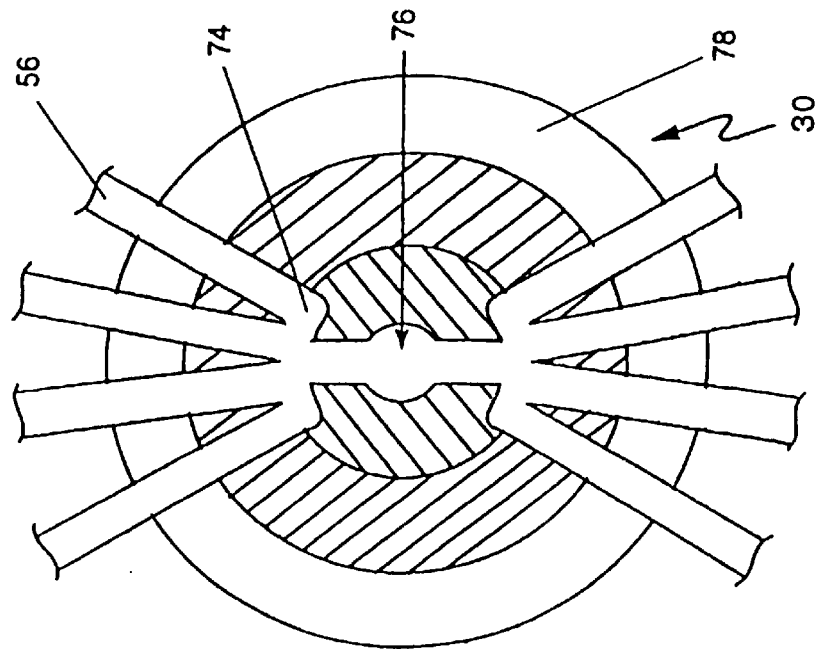
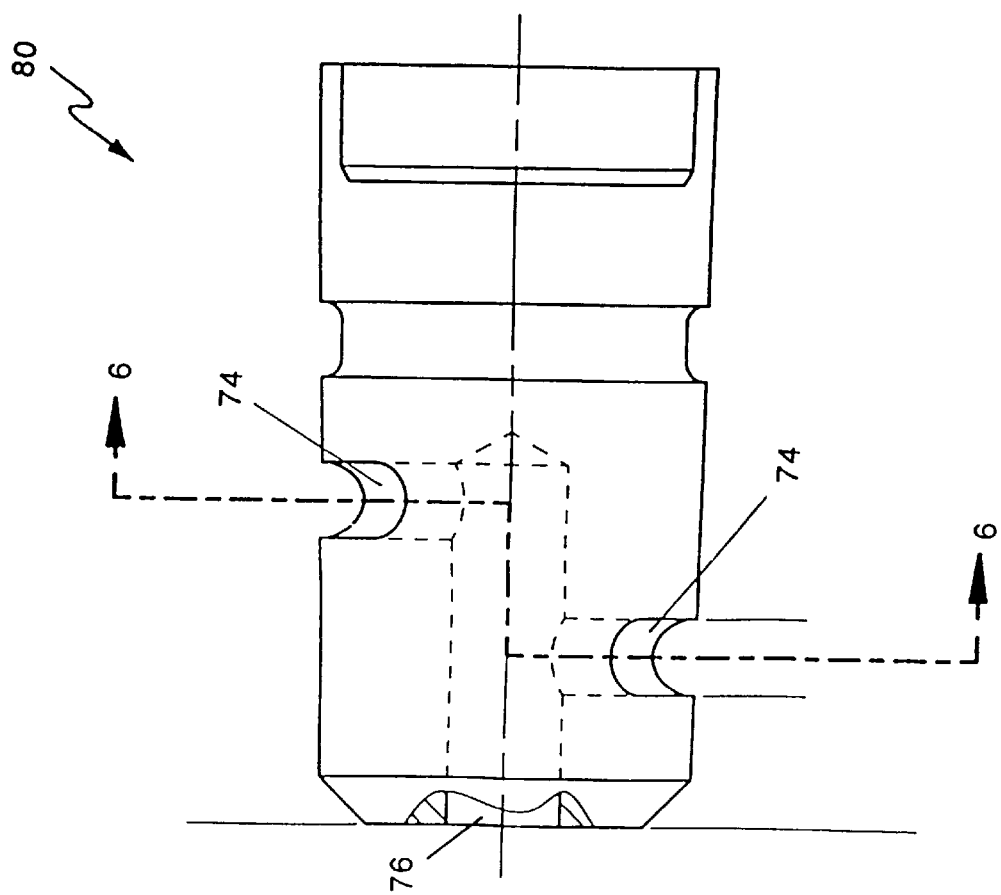
Fig. 6
Fig. 5

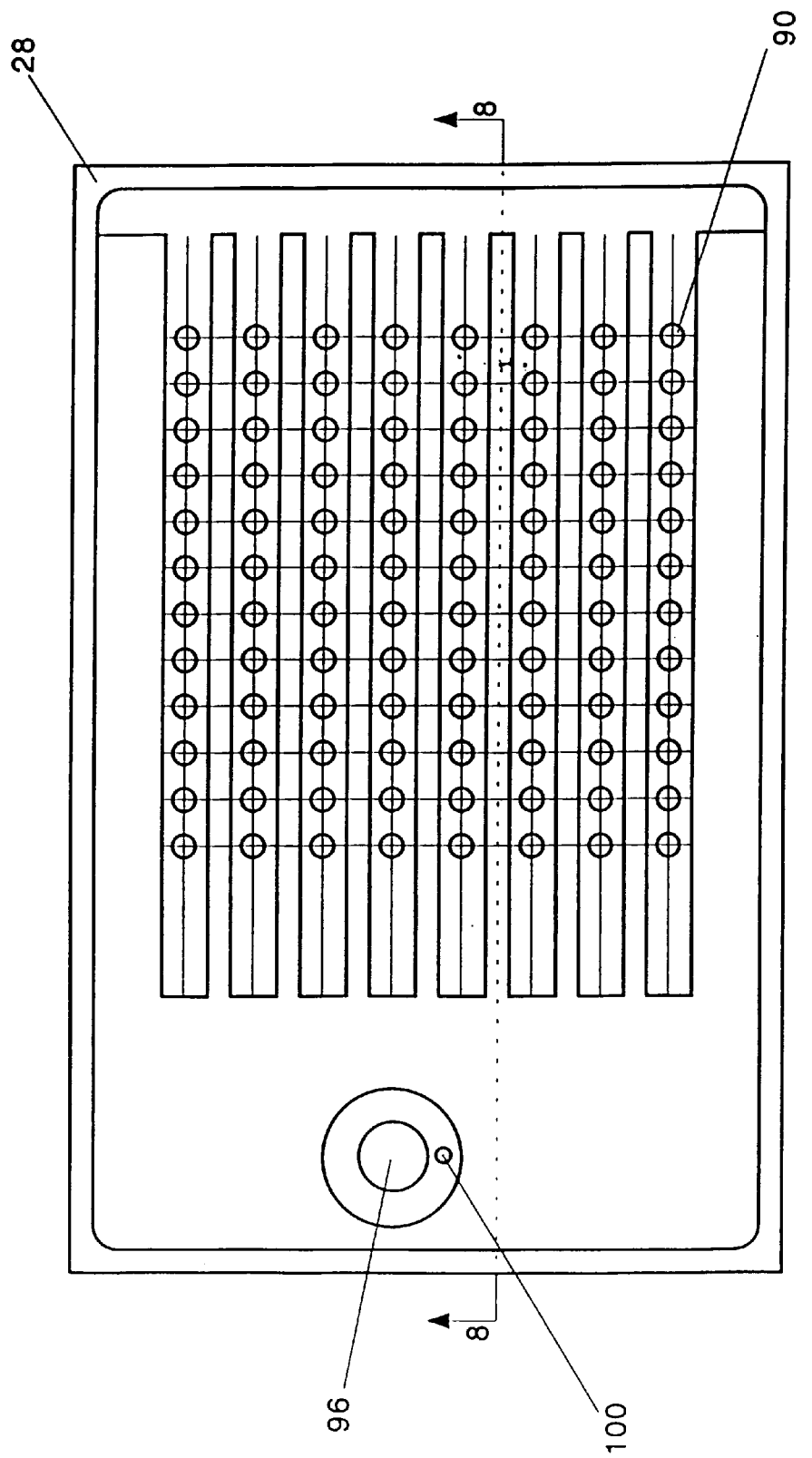

AUTOMATED ASSAYING DEVICE

FIELD OF THE INVENTION

The field of this invention relates generally to automated assaying devices. More particularly, the field of this invention relates to multi-port, multi-drive, multi-valve, assaying systems.

BACKGROUND OF THE INVENTION

In the past, assaying had been accomplished at first by means of manual pipetting and later by means of automated assaying machines. However, although the automation process has been supplemented over the years, further refinement has been desired. Certain problems exist, for instance, in automated assaying. In general, problems such as speed, numerosity of samples, contamination, and system flexibility are just a few of the problems that have continued to exist.

In particular, washing a reusable tip in the past has been quite problematic. Typically, disposable tips have been utilized to avoid the problem. However, limited attempts at washing in a wash basin have been attempted. The need exists for a thorough washing system integrated into an assaying system.

Another limitation of the prior art has been that, although varying number of probes have been provided to assay samples, there has been a distinct limitation as to the number of different fluids that can be sampled simultaneously by way of those probes. In fact, most, if not all, systems, only allow one fluid to be sampled at a time by any particular set of probes. If, however, a user desired to assay multiple solutions and aspirate or dispense varying volumes of those solutions by means of one set of probes, the task was generally not achievable. For instance, a single probe and tube system may be available in the prior art. Additionally, a system having eight tubes and probes may be available in the prior art to sample as well a single solution. Ninety-six probes and tubes may also be available in the prior art, but are limited again to their ability to carry out the single task of assaying a single solution in a single volumetric manner.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

U.S. PATENT DOCUMENTS

PATENT NO. ISSUE DATE INVENTOR

U.S No. 4,952,518 Aug. 28, 1990 Johnson, et al.
U.S No. 5,055,263 Oct. 8, 1991 Meltzer
U.S No. 5,114,681 May 19, 1992 Bertoncini, et al.
U.S No. 5,226,462 Jul. 13, 1993 Carl
U.S No. 5,262,128 Nov. 16, 1993 Leighton, et al.
U.S No. 5,306,510 Apr. 26, 1994 Meltzer
U.S No. 5,334,352 Aug. 21, 1994 Johnson
U.S No. 5,395,594 Mar. 7, 1995 Nokihara, et al.
U.S No. 5,497,670 Mar. 12, 1996 Carl
U.S No. 5,525,302 Jun. 11, 1996 Astle
U.S No. 5,531,959 Jul. 2, 1996 Johnson, et al.
U.S No. 5,660,792 Aug. 26, 1997 Koike OTHER PRIOR ART (Including Author, Title, Date, Pertinent Pages, Etc.) Packard, "MultiPROBE Robotic Liquid Handling Systems", December, 1996, entire brochure (12 pages).

The other prior art listed above, but not specifically discussed, teach other devices for sampling and further catalog the prior art of which the applicant is aware. These references diverge even more starkly from the references specifically distinguished above.

SUMMARY OF THE INVENTION

The present invention solves the multitude of problems presented in the automated assaying field. Overall, an automated system consisting of a plurality of lumens oriented in an array or matrix and controlled three-dimensionally by a robotic arm is provided. Such array is comprised of a plurality of rows and columns. Significantly, although the entire matrix may act as a single unit, each row may be acted upon individually and discretely.

More particularly, a system is disclosed which provides for a hydraulically controlled piping system. A hydraulic fluid, consisting of a water or wash or other solvent, is primed through a plurality of conduits and flushed through a series of syringes and thence into a plurality or multiplicity of lumens which are clustered and ganged and thereafter coupled to a matrix of probes. The ganged lumens are contained within a flexible tubing management tract. The tubing management tract is moveable by a three-dimensional robotic arm means. The tract contains an anti-lumen fouling means as a swivel within the tubing management tract.

By use of a computer operated programming system coupled to a controlling means and an array of motors coupled to the above-mentioned syringes, any particular row within the matrix of probes may be controlled individually. Furthermore, a computerized system may also three-dimensionally orient the array of probes to interface with a similarly and complimentarily arranged array of wells. Significantly, the entire system of tubing may be washed clean by running a wash through the entire system and into a complimentarily mated set of wells to wash not only the interior but also the exterior of the tips of the probes, which are preferably Teflon® coated.

OBJECTS OF THE INVENTION

It is an overall object of the present invention to provide an automated dispensation and aspiration system having an array or matrix of ports that are clusterably manipulable.

It is another object of the present invention to provide a three-dimensional robotic means of presenting such an array to a mateable array of wells.

It is another object of the present invention to provide an overall self-cleaning mechanism for such a system.

It is another object of the present invention to volumetrically control dispensation and aspiration within each such cluster.

It is another object of the present invention to provide or allow varying solutions or reagents to be utilized within each cluster of such array or matrix.

It is another object of the present invention to provide a means of preventing the lines or piping of the present invention from binding or kinking when manipulated in a three-dimensional space.

It is another object of the present invention to couple such a system to a computerized control means.

It is yet another object of the present invention to provide programmable control of each and every aspect of the system via the computerized control means.

It is another object of the present invention to provide a manifold for dividing the conduits of such a system without allowing cross-contamination of any such lines.

Viewed from a first vantage point, it is an object of the present invention to provide an automated assaying apparatus, comprising, in combination, a plurality of lumens sequestered into independently fed clusters and ganged into a bundle, three-dimensional moving means to orient the bundle, and fluid treatment means connected to the clusters to feed the clusters.

Viewed from a second vantage point, it is an object of the present invention to provide a method for assaying fluids, the steps including, placing a plurality of probes having a multiplicity of feed lines above a work surface, orienting a receiver on the work surface, addressing the receiver with the probes, and treating the probes with fluid provided by the receiver.

Viewed from a third vantage point, it is an object of the present invention to provide an automated assaying system, comprising, in combination, a plurality of fluid treatment means oriented in a matrix, the plurality of fluid treatment means oriented in clusters, and means to provide fluid to independent clusters.

Viewed from a fourth vantage point, it is an object of the present invention to provide an automated assaying system, comprising, in combination, a plurality of fluid treatment means oriented in a matrix, the plurality of fluid treatment means oriented in clusters, and means to purge the fluid treatment means for subsequent reuse.

Viewed from a fifth vantage point, it is an object of the present invention to provide a fluid sampling matrix, comprising, in combination, a robotic arm carrying the matrix, means to address the matrix to a work surface, and means to constrict rotation of the matrix vis-à-vis the work surface.

These and other objects will be made manifest when considering the following detailed specification when taken in conjunction with the appended drawing figures.

BRIEF DESCRIPTION OF THE DRAWINGS

FIG. 5 is a side view of the plug of the valve of FIGS. 3 and 4.

FIG. 6 is a cross-sectional view of the plug taken along line 6—6 of FIG. 5 and dedicated within the valve housing.

FIG. 7 is a top view of the wash basin.

DESCRIPTION OF PREFERRED EMBODIMENTS

Figure 1:
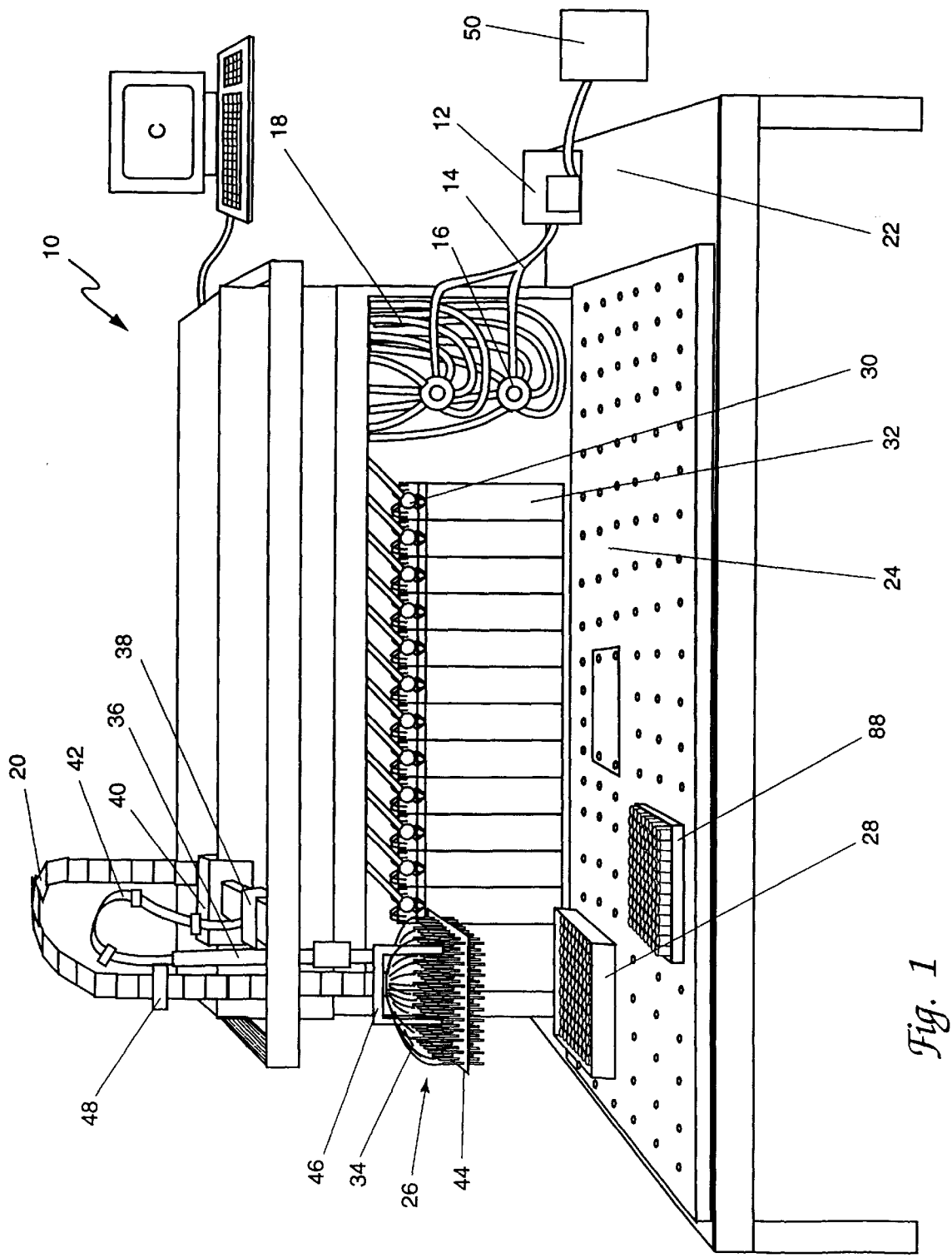
FIG. 1 is an overall perspective view of the invention.

Considering the drawings, wherein like reference numerals denote like parts throughout the various drawing figures, reference numeral 10 is directed to an automated assaying apparatus according to the present invention.

Figure 2:
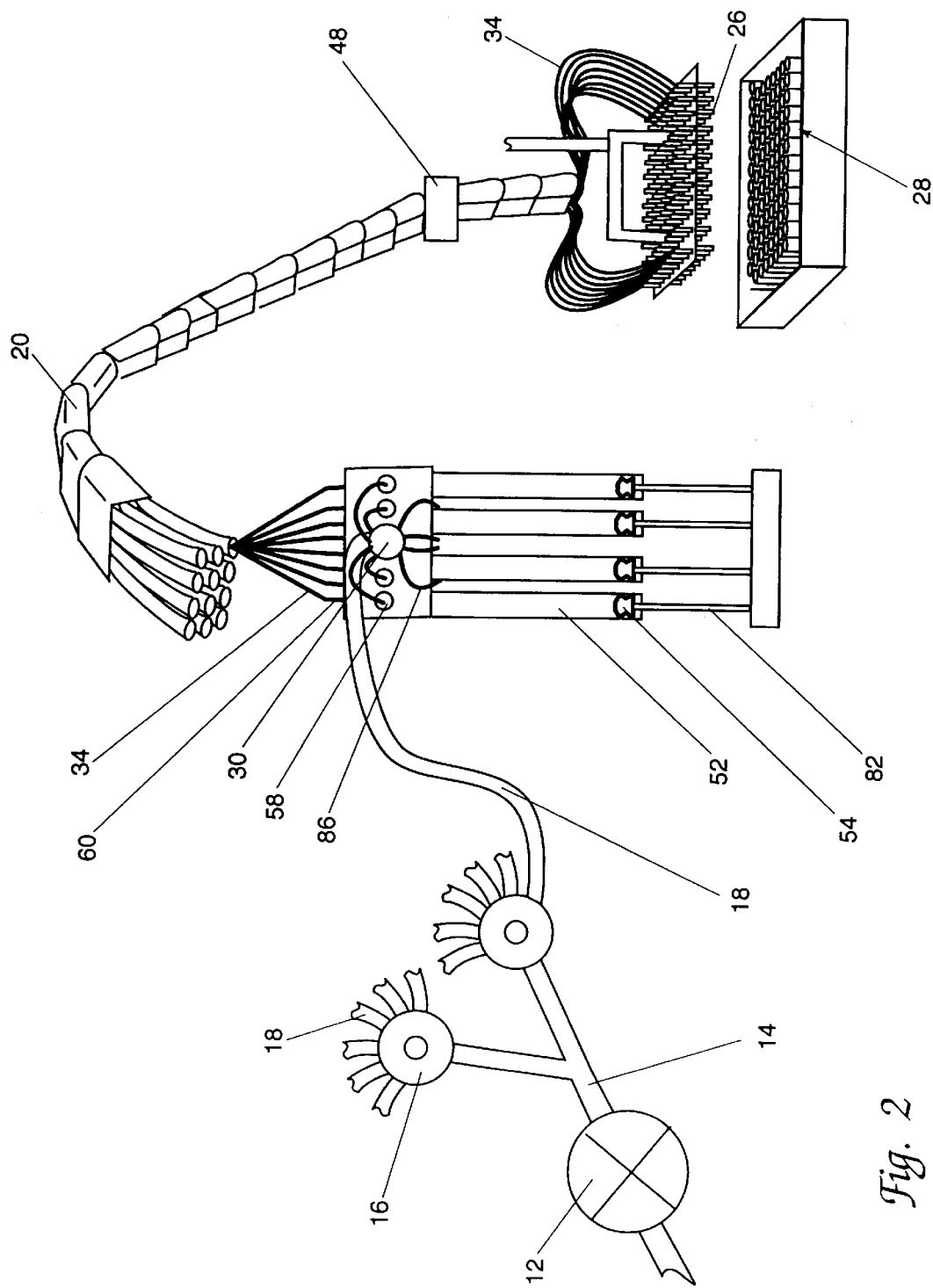
FIG. 2 is a schematic representation view of key elements of the invention.

Referring now to FIGS. 1 and 2, a description of the apparatus 10 will be hereafter provided. Commencing from a hydraulic solution source 50 which may contain any acceptable hydraulic solution, including water, sterile saline, solvent, or some other washing solution, a pump 12 is thereafter connected thereto. Pump 12 is preferably of the peristaltic type, however, any fluid-type pump may be employed, as will now be evident to those having ordinary skill in the art, informed by the present disclosure. Thereafter, from pump 12, a conduit 14 consisting of branch tubing coupled to, in this case, as depicted, two valves 16. The distribution valves 16 channel the wash fluid into a plurality of controllable cells 32. For example, as depicted, the distribution valves 16 provide output lines as arterial tubing 18 in equal numbers of six which spread to 12 of the housings 32 via a valve 30 on each housing 32.

FIGS. 3 through 6 provide further detail in regard to the syringe housings 32 and the valves 30. In particular, and continuing from the above, the feed lines 18 couple to valve 30. Valve 30 may be oriented in two positions by a motor 70 controllable by a computer controllable means or other appropriate user interface. A first orientation position will allow fluid to flow in though lines 18 from the wash through the valves 30 and through the entirety of the rest of the system. A second position would preclude further flow of fluid from lines 18 downstream toward the probes 26.

Figure 4:
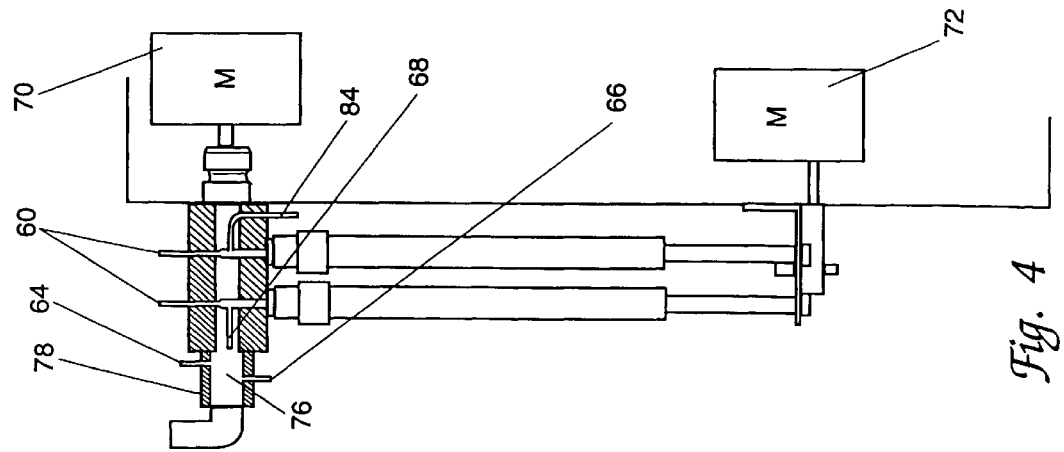
FIG. 4 is a side cross-sectional view taken along line 4—4 of the housing depicted in FIG. 3.
Figure 3:
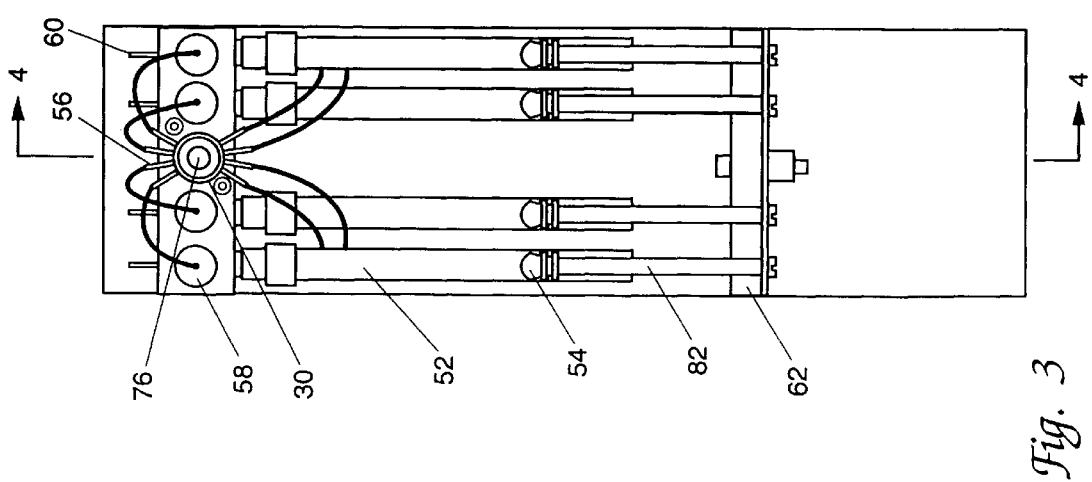
FIG. 3 is a front view of the syringe housing and valve of the present invention.
Figure 8:
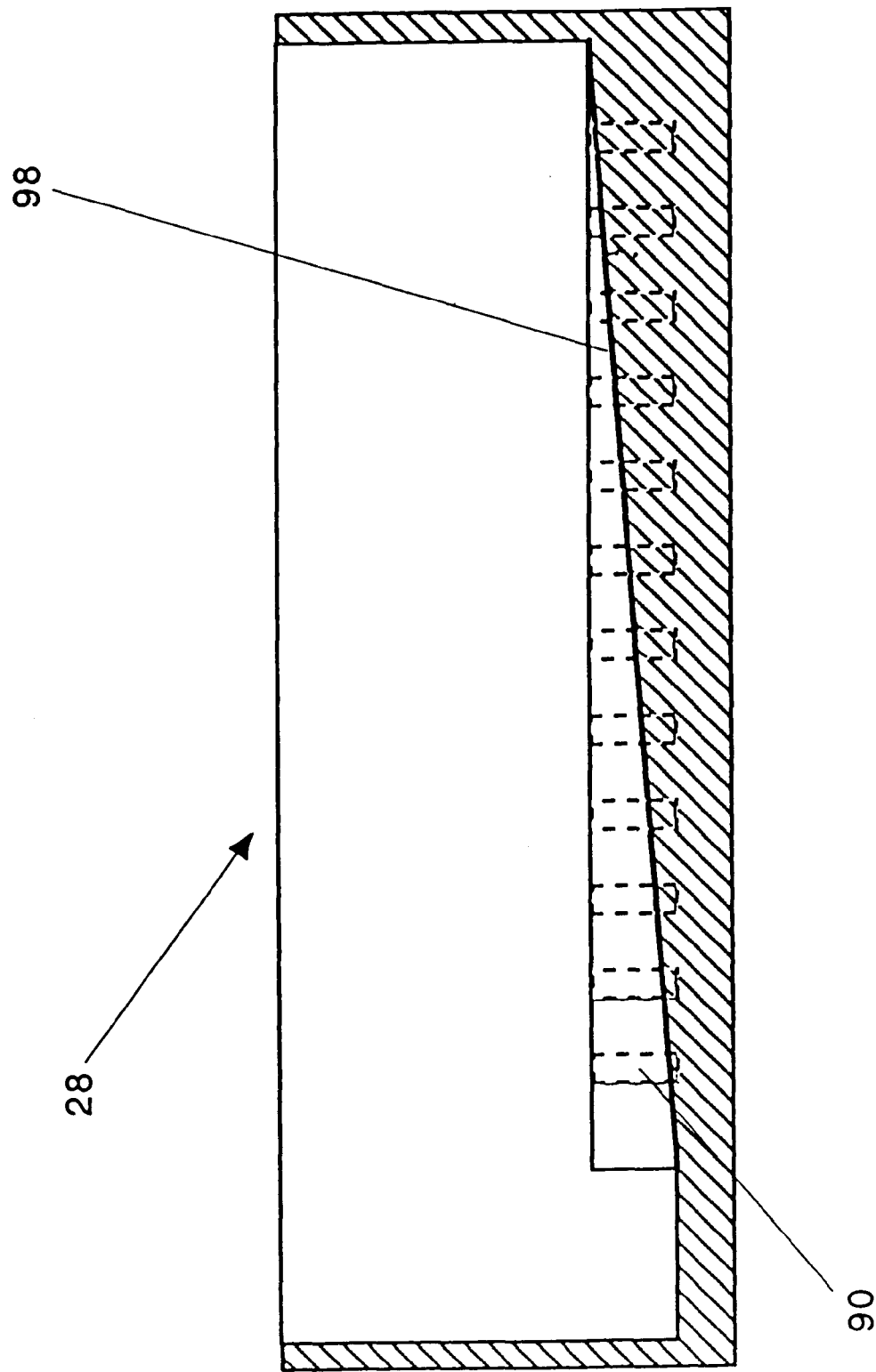
FIG. 8 is a side cross-sectional view taken along line 8—8 of FIG. 7.
Figure 9:
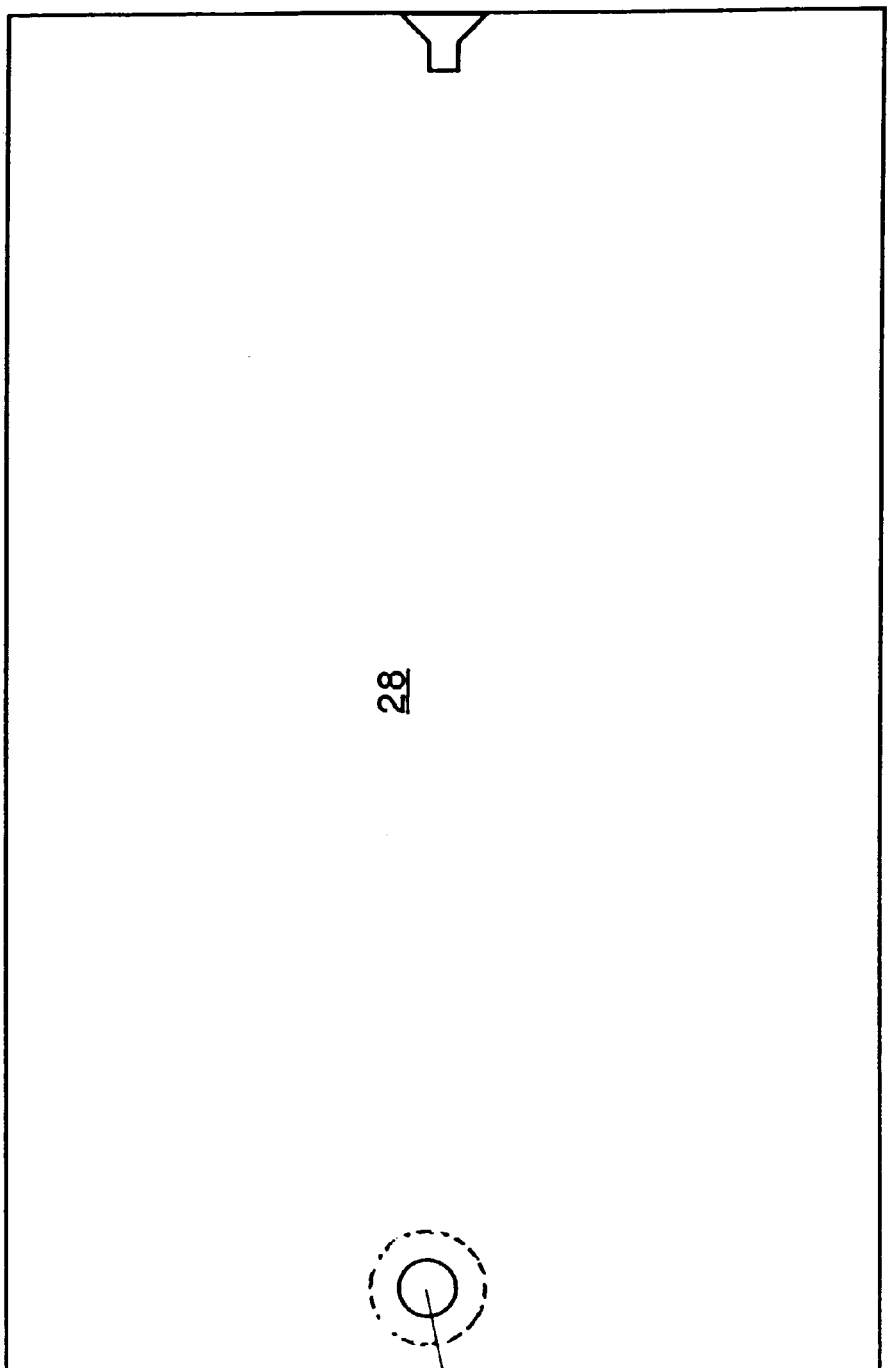
FIG. 9 is a bottom view of the wash basin.
Figure 10:
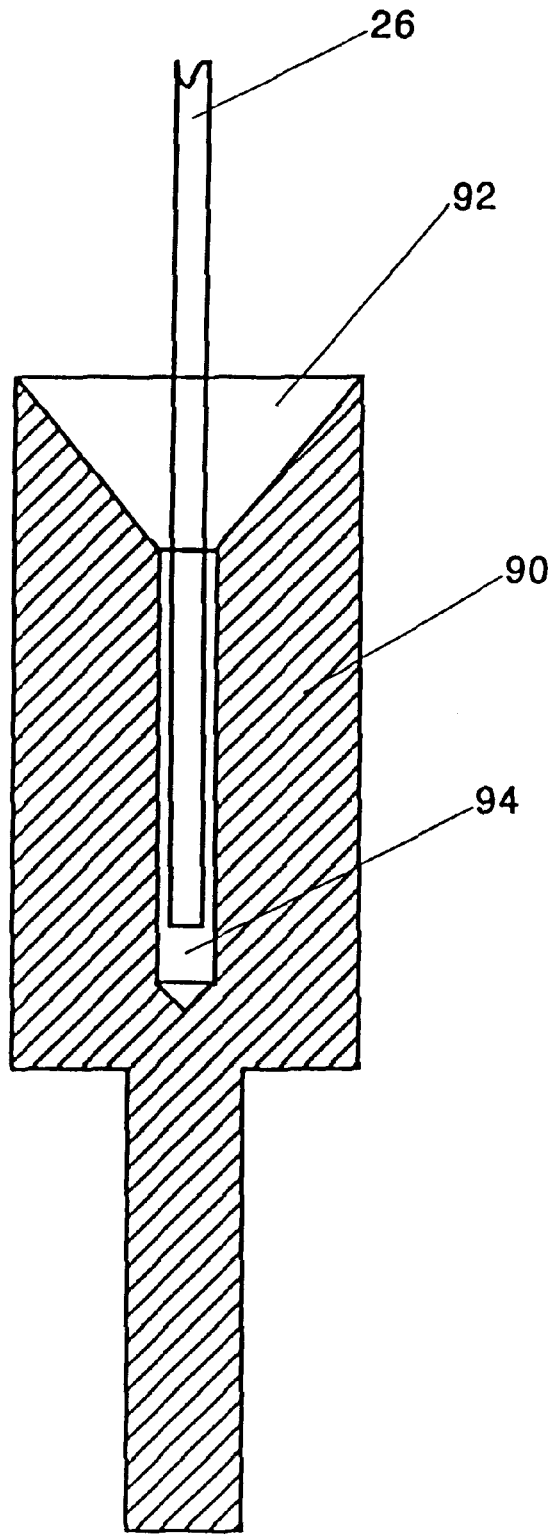
FIG. 10 is a side cross sectional view of a well with a probe inserted therein.

Fluid flowing into valve 30 via fluid port 76, while valve 30 is open to the entirety of the system, will thereafter flow into the eight spider ports 56 as depicted. Conduits 86 from four of the eight ports 56, such as 64, will then couple to a front set of four ports 58. Corollarily, the bottom four ports of the spider ports 56, in this case 66, will orient to a back set of four ports 58 which are downwardly protruding as shown in FIG. 4 to a tip 84. Those ports are internally coupled to syringes 52 by appropriately milled flow paths such as 68, which extend out to tips 60 and thereafter couple to lumens 34.

Syringes 52, of course, contain plungers 54 on plunger shafts 82. As there are eight syringes depicted in FIGS. 3 and 4, with four being to the front of the unit and four being to the rear, a plunger-pushing base 62 couples all of the syringe plunger shafts 82 together in any given unit. A motor 72, also coupled to a computer system, may specifically meter volumes via the syringes 52, either positively or negatively. That is, the plungers 54 may be pushed up to force fluid out of the system, or the plungers 54 may be drawn down to suction fluid into the system, both through probes 26.

As can be seen in FIGS. 4 through 6, the top spider ports 64 and the bottom spider ports 66 are slightly offset. This slight offset allows for the 180° rotation of an internal shaft 80 which acts as a valve key sleeve within an outer sleeve 78. That valve key sleeve 80, as depicted in FIGS. 5 and 6, contains, importantly, two grooves 74. While in an open position, those grooves orient with the spider ports 56. However, when those grooves 74 are rotated 180°, they no longer align with the spider ports 56, but instead a solid portion of the key sleeve 80 orients with those ports, closing them off from the wash system downstream. Therefore, when in a closed position, the system is controllable only by syringes 52 via motors 72, but not by pump 12. Importantly, each motor 72 may be individually controlled. Therefore, as depicted in FIG. 1, each of the twelve syringe housings 32, containing eight syringes and output ports, are individually controllable via a motor 72.

Thereafter, the lumens 34 extending from tips 60 are arranged as ganged clusters within tubing management housing 20. Tubing management housing 20 is preferably a flexible tract housing. Oriented with tubing management housing 20 is a swivel 48. Swivel 48 allows the upper portion of the tubing management housing 20 to slightly disorient or skew itself without binding of the lumens contained therein. That is, as tubing management housing 20 is moved about, swivel 48 allows that portion of tubing management housing 20 above swivel 48 to swivel freely so as not to foul. Tubing management housing 20 is also coupled to a three-dimensional robotic arm system, consisting of a vertical motion shaft 36, lateral motion couple 38 and longitudinal motion sleeve 40. The vertical motion shaft 36 is coupled at an upper portion to the management tubing 20, slightly below the swivel 48, and then at a lower portion to a U-shaped bracket 46.

Thereafter, the bracket 46 is coupled to a probe mount 44 having a matrix or array of probes 26 projecting therethrough. The ganged cluster of a multiplicity of lumens projecting through tubing management tract 20 are thereafter coupled to the probes 26. Probes 26 are preferably Teflon® coated to prevent sticking of unwanted contaminants, and thereby preclude contamination when properly washed. The probes 26 are also preferably removably coupled to the lumens 34 so that varying sizes may be utilized as needed. They are coupled in such a fashion that the groups of eight which started from each syringe housing 32 are again oriented together in rows in this matrix. Color coding each row of eight would further provide greater ease of use. One other advantage of such a clustered system is in the event of hydraulic difficulty, individual modules may be examined, as opposed to the entire system.

A complimentarily formed array of wells 88 are provided thereunder on a matrix unit 24 upon table 22. A computer controlled system C coupled to system 10 and motor means may orient the robotic arm of the three-dimensional apparatus and present the array of probes to the array of wells as desired. The array of wells may contain reagents, wash, reactants, solvents, or any other desired fluids. As depicted in FIG. 1, there are 96 probes oriented on the probe mount 44. Depicted is an array having twelve columns and eight rows, wherein each row of eight is individually and discretely controllable. Also depicted is a deep wash well 28, for washing the probes therein.

With regard to the deep wash well 28, as depicted in FIGS. 7 through 10, a matrixed, drainable basin 28 is depicted. Basin 28 is perhaps described as a trough having a sloped bottom surface 98 and a matrix of wells 90 bored therethrough and projecting therefrom. A drain 96 having an orienting indicia 100 is located as the extreme downward end of the sloping base 98. Individual wells 90, of course, contain a bore 94 and a mouth 92. Bore 94 is for receiving a probe 26. As the bore 94 and mouth 92 fill with fluid, that overflowing fluid will drain downward along the inclined bottom surface 98 to the drain 96. In this manner, contaminated fluids may be removed from the well and contaminants may be cleansed from the probes.

Figure 11:
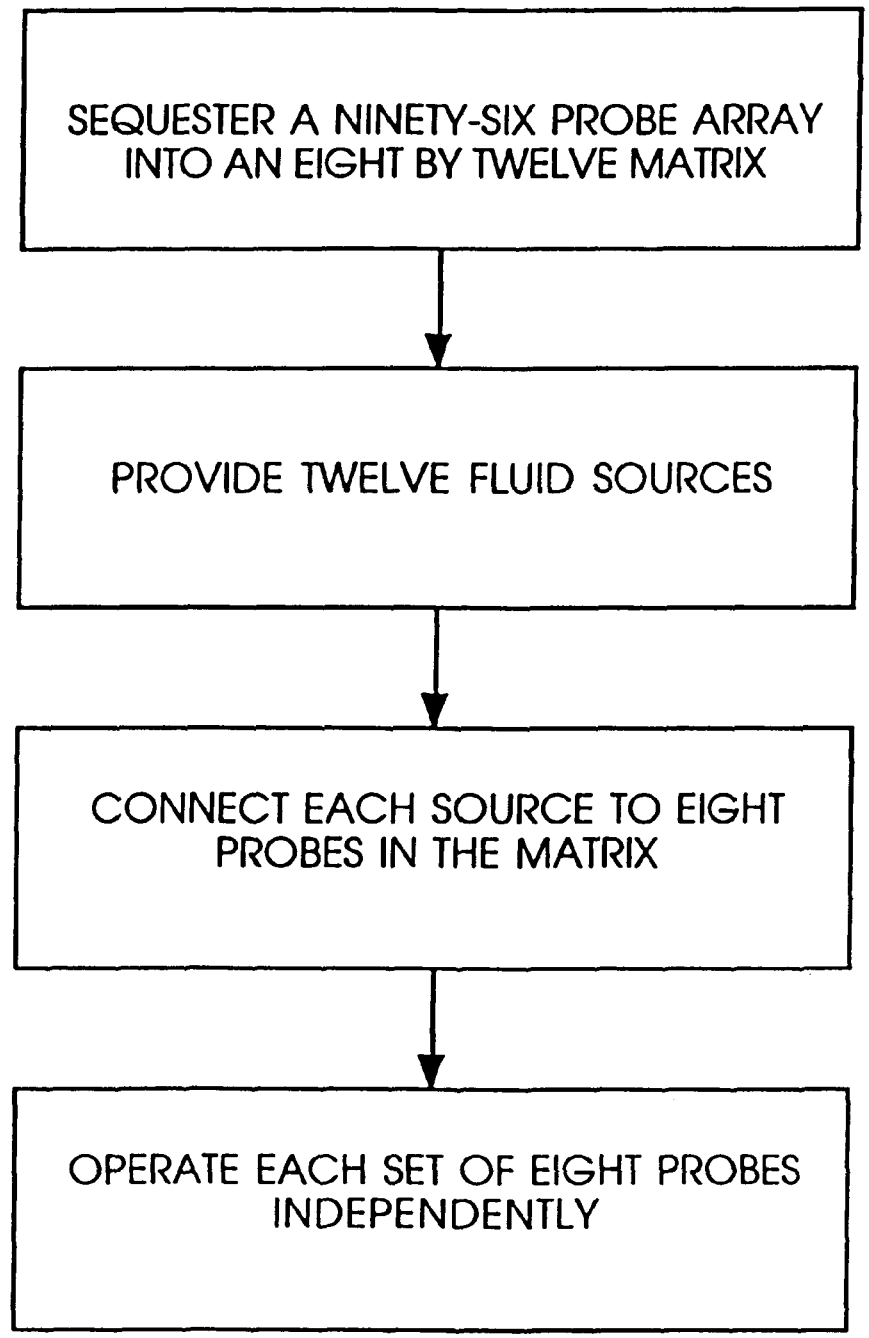
FIG. 11 is a flow diagram of a particular method of the invention.
Figure 12:
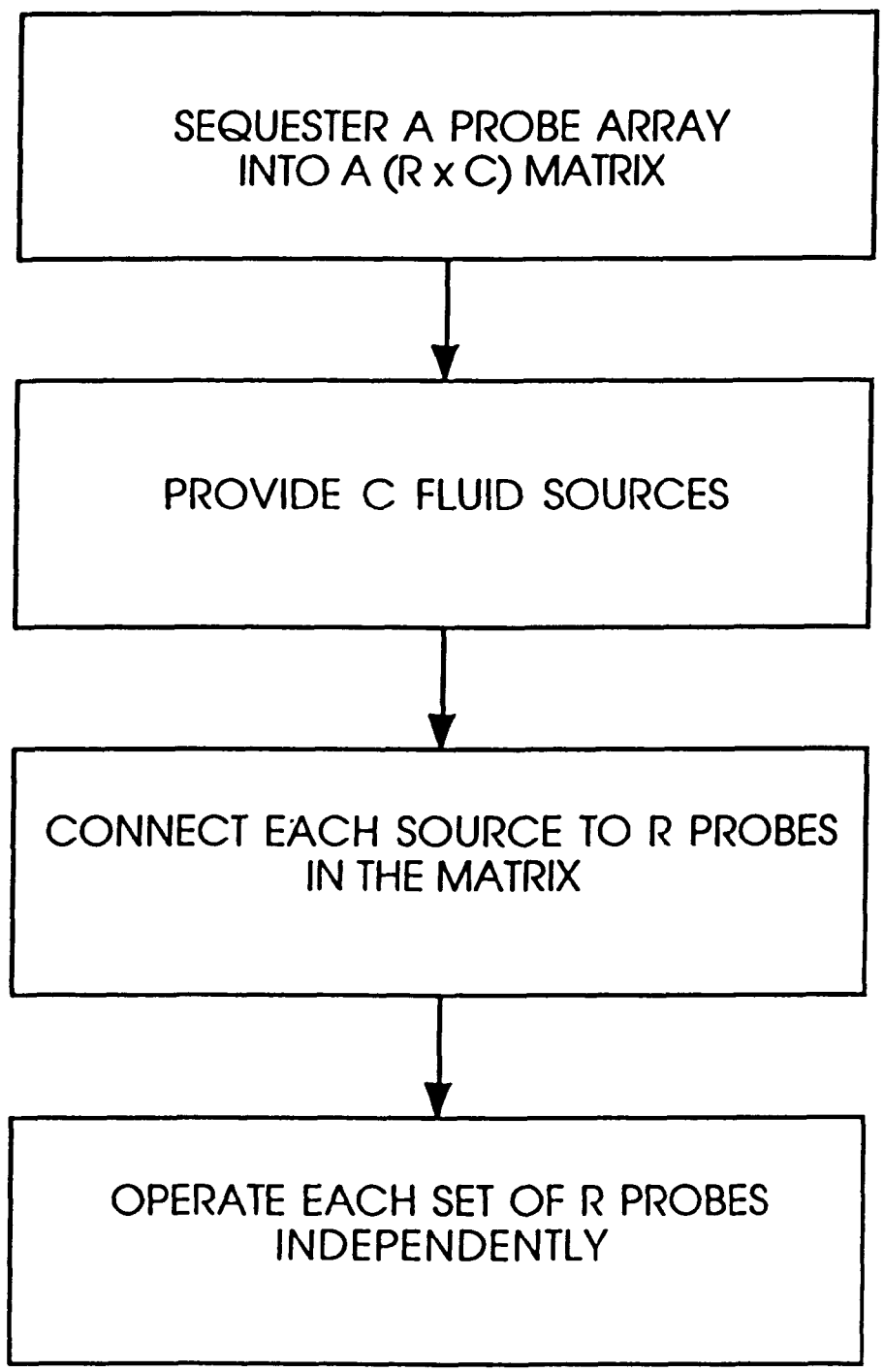
FIG. 12 is a flow diagram of a general method of the invention.

In use and operation, as broadly depicted in FIGS. 11 and 12, one would generally first wish to fill the tubular system with a fluid from source 50 to so prime the system for hydraulic manipulation by orienting the valves 30 in an open position; this may be accomplished via pump 12. Once the system is filled with fluid, the pumping of pump 12 may be stopped. Thereafter, valves 30 are turned 180° by motors 70 so that the syringes may alone control the system. As will now be understood, wash fluid will now be situated at the tips of the probes 26. To avoid contamination or commingling of the wash fluid with any fluids contained within the wells 88 for sampling, a small air bubble may be drawn into the tips of the probe at this time by slightly drawing all of the syringes to aspirate ambient air. Now fluids may be drawn from the wells 88 as desired. Thereafter, those fluids drawn from wells 88 may be dispensed into another set of wells elsewhere on table 22 by manipulation of the robotic three-dimensional motion means. When it is desired to rewash the system for a new analysis, the array of probes 26 may be oriented into the deep well wash 28. By now opening valves 30 again, wash fluid may be drawn from source 50 through pump 12 through the entire system and the probe tips 26 will be washed by said fluid. As the washing fluid is drawn through the system, each cone in the deep well wash matrix is continually overfilled. The contaminated fluids are then evacuated to a waste container. In this manner, not only is the interior of the probe cleansed, but the exterior of the probe tips likewise cleansed. This is desirable in that it precludes the necessity of replacing probe tips.

The individual and discrete dispensation or aspiration will now be further described. As each of the syringe housings and sets 32 are individually controllable by motors 72, it should now be understood that a single motor 72 may push a set of eight plungers upward to cause dispensation in one row while another set of eight plungers may be forced upward a varying distance to cause a differing volumetric dispensation. The reverse is also true for aspiration purposes. Furthermore, it is clear that a multitude of syringe sizes may be utilized. For instance, it is certainly envisioned that at the very least, standard syringe sizes such as 50, 100, 250, 500 or 1000 microliters may be utilized in sets in any of the desired housings 32. And of course, although twelve sets of housings are depicted, providing for eight output ports and thereafter ninety-six lumens and probes, the systems can easily be sized upwards or downwards as necessitated.

Furthermore, although a rectangular matrix is depicted, other geometrical arrays may similarly be utilized, such as a hexagonal array having six triangle clusters associated therewith and say ten probes per cluster. This of course would provide a total of sixty probes, and ten spider ports on six housings 32.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An automated assaying apparatus, comprising, in combination:
    a plurality of lumens sequestered into independently fed clusters and ganged into a bundle;
    three-dimensional moving means to orient said bundle;
    fluid treatment means connected to said clusters to feed said clusters
wherein said fluid treatment means includes a fluid pump and a fluid source delivering fluid to said pump and a plurality of valves, one valve per said cluster, coupled between said clusters and said pump and each said valve operatively coupled to one syringe housing having a plurality of syringes therein.

2. The apparatus of claim 1 wherein said valve comprises:
    a fluid port to receive fluid from said pump,
    an outer sleeve which circumscribes said fluid port, and
    an internal shaft residing within said outer sleeve and acting as a valve key sleeve and having fluid transferring grooves which deliver or prevent fluid to pass into each said syringe in its respective said syringe housing via interposed outlet ports which are alternatively aligned or obstructed based on orientation of said grooves.

3. The apparatus of claim 2 wherein there are two said grooves, each of which feed four said syringes-through said outlet ports.

4. The apparatus of claim 3 wherein four said outlet ports are located above and four said outlet ports below said outer sleeve, said above outlet ports offset from said below outlet ports allowing 180° rotation of said internal shaft for fluid admission/preclusion.

5. The automated assaying apparatus of claim 2 wherein said plurality of syringes are oriented one syringe per lumen.

6. The automated assaying apparatus of claim 5 wherein said fluid treatment means includes a first plurality of motors, one operatively coupled to each said valve, and a second plurality of motors, one operatively coupled to said plurality of syringes within said syring housing.

7. The automated assaying apparatus of claim 6 further comprising a plurality of probes removably coupled to an end of said lumens.

8. The automated assaying apparatus of claim 7 wherein said fluid treatment moans includes wash means for cleansing said lumens and probes.

9. The automated assaying apparatus of claim 8 further comprising lumen management means for flexibly containing said bundle.

10. The automated assaying apparatus of claim 9 further comprising swivel means coupled to said lumen management means for ensuring lumen integrity during movement by said three-dimensional moving means.

11. The automated assaying apparatus of claim 10 further comprising a plurality of probe receiving means for sequestering samples oriented in an operatively spatial relationship to said probes.

12. The automated assaying apparatus of claim 11 wherein said wash means includes a trough containing a plurality of probe receiving means and drainage means operatively coupled to said trough.

13. The automated assaying apparatus of claim 12 wherein said probes and said probe receiving means are oriented into complementary matrices.

14. A method for assaying fluids, the steps including:
placing a plurality of probes having a multiplicity of feed lines above a work surface;
sequestering the probes and feed lines into clusters
orienting a receiver on the work surface;
addressing the receiver with the probes;
independently treating the probes in clusters with fluid provided by the receiver;
loading the clusters of probes with fluid by interposing clusters of syringes between the probes and a fluid;
and valving fluid into the syringes in the clusters, one value per cluster.

15. The method of claim 14 wherein said valving includes:
fluid porting to receive fluid,
pumping fluid therethrough forming the valve as an outer sleeve which circumscribes the fluid porting, and
placing an internal shaft within said outer sleeve and acting as a valve key sleeve and having fluid transferring grooves which deliver or prevent fluid to pass into syringes in a respective syringe housing via interposing outlet ports and alternatively aligning or obstructing the outlets based on orientation of grooves formed in the sleeve.

16. The method of claim 15 further comprising the step of precluding feed line fouling.

17. The method of claim 16 further comprising the step of orienting the probes within a wash basin and washing the probes.

18. An automated assaying system, comprising, in combination:
a plurality of fluid treatment means oriented in a matrix;
said plurality of fluid treatment means oriented in clusters; and
means to provide fluid to independent clusters via a plurality of valves, one valve per cluster, wherein said valve comprises:
a fluid port to receive fluid from said pump,
an outer sleeve which circumscribes said fluid port, and
an internal shaft residing within said outer sleeve and acting as a valve
key sleeve and having fluid transferring grooves which deliver or prevent fluid to pass into a syringe in its respective syringe housing via interposed outlet ports which are alternatively aligned or obstructed based on orientation of said grooves.

19. The automated assaying system of claim 18 further comprising a complementarily formed matrix of wells oriented on a table top.

20. The automated assaying system of claim 19 wherein said plurality of syringes are oriented one per said fluid treatment means.

21. The automated assaying system of claim 20 wherein said matrix includes robotic means for moving said matrix in three dimensions above said table.

22. An automated assaying system, comprising, in combination:
a plurality of fluid treatment means oriented in a matrix;
said plurality of fluid treatment means oriented in clusters each said cluster controlled by one valve communicating with syringes in a syringe housing wherein said valve comprises:
a fluid port to receive fluid from said pump,
an outer sleeve which circumscribes said fluid port, and
an internal shaft residing within said outer sleeve and acting as a valve key sleeve and having fluid transferring grooves which deliver or prevent fluid to pass into each said syringe in its respective said syringe housing via interposed outlet ports which are alternatively aligned or obstructed based on orientation of said grooves; and
means to purge said fluid treatment means for subsequent reuse.

23. A fluid sampling matrix, comprising, in combination:
a robotic arm carrying said matrix;
said matrix coupled to a plurality of lumens ganged in clusters, each said cluster communicating with one syringe housing supporting a plurality of syringes, one per lumen, a valve per syringe housing operable to deliver or preclude fluid to each said syringe in said syringe housing, wherein said valve comprises:

a fluid port to receive fluid from said pump, an outer sleeve which circumscribes said fluid port, and an internal shaft residing within said outer sleeve and acting as a valve key sleeve and having fluid transferring grooves which deliver or prevent fluid to pass into each said syringe in its respective said syringe housing via interposed outlet ports which are alternatively aligned or obstructed based on orientation of said grooves;

means to address said matrix to a work surface; and means to constrict rotation of the matrix vis-à-vis said work surface.

* * * * *